United States Patent
Liu et al.

(10) Patent No.: US 11,744,841 B2
(45) Date of Patent: Sep. 5, 2023

(54) USE OF TREZASTILBENOSIDE IN MANUFACTURE OF PRODUCT FOR TREATING AND/OR PREVENTING DISEASE OF RESPIRATORY SYSTEM

(71) Applicant: KPC PHARMACEUTICALS, INC., Yunnan (CN)

(72) Inventors: Yidan Liu, Yunnan (CN); Xujuan Yang, Yunnan (CN); Xi Huang, Yunnan (CN); Qing Huang, Yunnan (CN); Shuixian Zhao, Yunnan (CN); Guoguang Liu, Yunnan (CN); Jianhua Shang, Yunnan (CN)

(73) Assignee: KPC PHARMACEUTICALS, INC., Yunnan (CN)

( * ) Notice: Subject to any disclaimer, the term of this patent is extended or adjusted under 35 U.S.C. 154(b) by 4 days.

(21) Appl. No.: 17/136,282

(22) Filed: Dec. 29, 2020

(65) Prior Publication Data

US 2021/0196736 A1 Jul. 1, 2021

(30) Foreign Application Priority Data

Dec. 30, 2019 (CN) .......................... 201911391840.4

(51) Int. Cl.
*A61K 31/7034* (2006.01)
*A61P 11/14* (2006.01)

(52) U.S. Cl.
CPC .......... *A61K 31/7034* (2013.01); *A61P 11/14* (2018.01)

(58) Field of Classification Search
CPC .... A61K 31/7034; A61K 36/708; A61P 11/14
See application file for complete search history.

(56) References Cited

FOREIGN PATENT DOCUMENTS

| CN | 101787061 | | 7/2010 |
|---|---|---|---|
| CN | 103505468 | | 1/2014 |
| CN | 104758303 A | * | 1/2014 |
| EP | 2862575 | | 4/2015 |

OTHER PUBLICATIONS

English machine translation of CN 104758303A, published Jan. 2014 (Year: 2014).*
Jun, H. et al., Phytomedicine, "Discovery and identification of quality markers of Chinese medicine based on pharmacokinetic analysis", 2018, vol. 44, pp. 182-186 (Year: 2018).*
Malik, M. et al., International Journal of General Medicine and Pharmacy, 2016, vol. 5, No. 4, pp. 35-44 (Year: 2016).*
Dicpinigaitis, P.V. et al., Pharmacological Reviews, "Antitussive Drugs-Past, Present, and Future", 2014, vol. 66, pp. 468-512 (Year: 2014).*

* cited by examiner

*Primary Examiner* — Bahar Craigo
(74) *Attorney, Agent, or Firm* — BakerHostetler

(57) ABSTRACT

The present disclosure belongs to the biopharmaceutical field, and discloses uses of Trezastilbenoside in manufacture of a product for treating and/or preventing a disease of respiratory system, and particularly uses of Trezastilbenoside in manufacture of a product for treating and/or preventing a disease of respiratory system with symptoms of cough and/or expectoration and/or asthma. As indicated by the test results of the present disclosure, Trezastilbenoside has significant efficacy of relieving cough, eliminating phlegm, relieving asthma and anti-inflammation, and has a potential therapeutic effect on respiratory system diseases, thus possessing broad prospects in clinical application.

5 Claims, No Drawings

USE OF TREZASTILBENOSIDE IN MANUFACTURE OF PRODUCT FOR TREATING AND/OR PREVENTING DISEASE OF RESPIRATORY SYSTEM

CROSS REFERENCE TO RELATED APPLICATION

The present application claims priority to Chinese Patent Application No. 201911391840.4, titled "USE OF TREZASTILBENOSIDE IN MANUFACTURE OF PRODUCT FOR TREATING AND/OR PREVENTING DISEASE OF RESPIRATORY SYSTEM", filed on Dec. 30, 2019 with the Chinese Patent Office, which is incorporated herein by reference in its entirety.

FIELD

The present disclosure belongs to the technical field of medicine, and specifically relates to the application of Trezastilbenoside in the manufacture of a product for treating and/or preventing a disease of respiratory system, which particularly has remarkable efficacy in the aspect of treating cough, phlegm and asthma.

BACKGROUND

Respiratory system diseases are common and frequently-occurring diseases, mainly causing pathological changes in trachea, bronchus, lung and thoracic cavity, and occur as, at most of time, cough, asthma, breathing disorder and excessive phlegm, which affects patient health seriously and even endanger a patient's life. They are the third cause of mortality rate in cities, while the leading cause in rural areas. Moreover, it should be noted that the incidence of and the mortality rate caused by the chronic obstructive pulmonary disease (abbreviate as COPD, including chronic bronchitis, emphysema and pulmonary heart disease), bronchial asthma, lung cancer, pulmonary diffuse interstitial fibrosis as well as other diseases like pulmonary infection, keep on increasing both at home and abroad, due to air pollution, smoking, aging population and other causes.

In recent years, the incidence of respiratory diseases is also increasing due to the trend in aging society and the aggravation of environmental pollution. The crucial point of treating the respiratory diseases is to cure cough, phlegm and asthma which are the most common clinical symptoms of such diseases. In the clinical treatment, medicines for anti-inflammation, antivirus, antianaphylaxis, spasmolysis and asthma, etc., have been mostly applied, but their efficacy is unsatisfying, they only can eliminate the symptoms rather than cure the diseases fundamentally, and they also produce various side effects. A long-term use is prone to cause medicine resistance, reoccurring, as well as a series of complications outside the respiratory system, such as dizziness, palpitation, hypodynamia, anorexia, edema of both lower limbs and other symptoms. Moreover, the symptomatic treatment using antibiotics, antiviral agents and other drugs is prone to cause an appearance of bacteria, viruses and drug-resistant strains as well as dysbiosis in organisms. Such drug (antibiotics and hormones) abuse has caused more and more iatrogenic diseases, which brings economic loss and physical and mental suffering to patients. Cough, phlegm and asthma can occur independently or simultaneously, and may affect each other. Therefore, it is necessary to develop a drug, which has efficacy for relieving cough, eliminating phlegm and relieving asthma while producing less toxic side effects.

Trezastilbenoside ((E)-1-(3,5-dihydroxyphenyl)-2-β-hydroxy-4-O-β-D-glucopyranosephenyl)ethylene or 3,5,3',4'-trihydroxystibene-3'-O-β-glucoside) has a plant source of the rhizome of *Rheum lhasaense* A. J. Li et P. K. Hsiao. As suggested from the researches, Trezastilbenoside has activities of anti-inflammation, anti-oxidation, free radical scavenging and the like. As suggested from the safety researches, Trezastilbenoside had good safety, since no toxic side reactions and death occurred in acute toxicity tests, and no chromosome aberrations or mutagenesis were found in the genetic test. The structural formula of Trezastilbenoside is shown in Formula I:

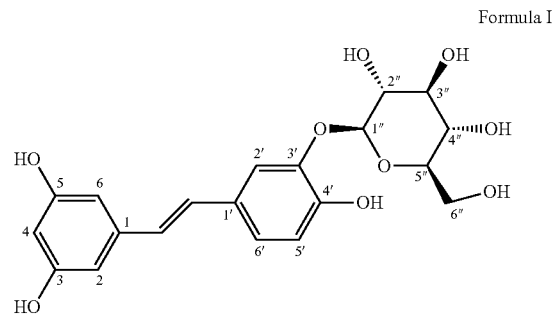 [SMILES: OC[C@H]1O[C@@H](Oc2cc(/C=C/c3cc(O)cc(O)c3)ccc2O)[C@H](O)[C@@H](O)[C@@H]1O]

Formula I

Chinese Patent Application No. 201010116358.2 discloses use of Trezastilbenoside in preparation of a formulation for treating and preventing cardio-cerebro ischemia diseases and preparation method thereof. Chinese Patent Application No. 201210198159.X discloses use of a stilbene compound in manufacture of a medicament for preventing and treating depression. Chinese Patent Application No. 201210202957.5 relates to use of Trezastilbenoside in manufacture of a medicament for improving microcirculatory disorders, and discloses extraction processes and measurement methods for Trezastilbenoside. The prior art shows that Trezastilbenoside has activities of treating and preventing ischemia cardio-cerebrovascular disease, anti-depression and improving microcirculation, but there is no report on its use as the medicine for cough, phlegm and asthma.

In view of that, the present disclosure is provided.

SUMMARY

In order to solve the technical problems and overcome the disadvantage of the prior art, the present disclosure provides use of Trezastilbenoside in manufacture of a product for treating and/or preventing a respiratory system disease, which is particularly suitable for a respiratory system disease with symptoms of cough, phlegm and asthma.

The technical solutions with the following basic concepts are adopted by the present disclosure, so as to solve the technical problem described above.

The first object of the present disclosure is to provide use of Trezastilbenoside in manufacture of a product for treating and/or preventing a respiratory system disease.

Said Trezastilbenoside in the present disclosure may be a Trezastilbenoside extract, or the pure Trezastilbenoside compound. The preparation method of Trezastilbenoside may refer to the Chinese Patent Application No. 201010116358.2.

The present disclosure discloses new medical applications of Trezastilbenoside. In the present disclosure, it was found from experiments that Trezastilbenoside can significantly reduce the number of coughs in mice induced by concentrated ammonia, significantly reduce the number of coughs in guinea pigs induced by citric acid and prolong the cough latency, significantly increase the excretion amount of phenol red from the mouse trachea, significantly prolong the asthma latency in guinea pigs induced by histamine phosphate and acetylcholine chloride, and significantly inhibit the degree of ears swelling in mice. As suggested from the test results of the present disclosure, Trezastilbenoside has remarkable efficacy of relieving cough, eliminating phlegm, relieving asthma and antiinflammation, and has potential curative effects on respiratory system diseases. The active ingredient of the present disclosure can be extracted from plants, the drug material employed is cheap and easily available, and the market prospects are promising.

The second object of the present disclosure is to provide use of Trezastilbenoside in manufacture of a product for treating and/or preventing a respiratory system disease with a cough symptom.

In a further embodiment, the cough symptom is induced by inhalation or by respiratory tract infection.

As shown from the experiment results of the present disclosure, Trezastilbenoside is capable of significantly reducing the number of coughs in mice induced by concentrated ammonia, and significantly reducing the number of coughs in guinea pigs induced by citric acid and prolonging the cough latency, indicating that Trezastilbenoside has remarkable efficacy of relieving cough.

The third object of the present disclosure is to provide use of Trezastilbenoside in manufacture of a product for treating and/or preventing a respiratory system disease with symptoms of cough and phlegm.

As shown from the experiment results of the present disclosure, Trezastilbenoside is capable of significantly increasing the excretion amount of phenol red from the mouse trachea, indicating that Trezastilbenoside has a remarkable efficacy of eliminating phlegm.

The fourth object of the present disclosure is to provide use of Trezastilbenoside in manufacture of a product for treating and/or preventing a respiratory system disease with a symptom of panting or asthma.

As shown from the experiment results of the present disclosure, Trezastilbenoside is capable of significantly prolonging the asthma latency of guinea pig induced by histamine phosphate and acetylcholine chloride, indicating that Trezastilbenoside has an efficacy of relieving asthma.

In a further embodiment, the product includes a food product, a health product and a medicament.

In a further embodiment, the product for treating and/or preventing a respiratory system disease is a medicament, comprising Trezastilbenoside and a pharmaceutically acceptable adjuvant.

In a further embodiment, the medicament is provided as various acceptable dosage forms.

Preferably, the dosage forms include injections, tablets, capsules, powders, pills, oral solutions or suspensions.

The fifth object of the present disclosure is to provide a product for treating and/or preventing a respiratory system disease, wherein the product comprises an active ingredient of Trezastilbenoside.

In this embodiment, the product for treating and/or preventing a respiratory system disease comprises active ingredients containing Trezastilbenoside, and may be in form of a food product, a health product or a medicament.

Preferably, the product is a medicament, comprising Trezastilbenoside and a pharmaceutically acceptable adjuvant.

By adopting the technical solutions described above, the present disclosure produces the following beneficial effects as compared to the prior art.

1. The present disclosure discloses new medical applications of Trezastilbenoside. In the present disclosure, it was found from experiments that Trezastilbenoside can significantly reduce the number of coughs in mice induced by concentrated ammonia, significantly reduce the number of coughs in guinea pigs induced by citric acid and prolong the cough latency, significantly increase the excretion amount of phenol red from the mouse trachea, significantly prolong the asthma latency in guinea pigs induced by histamine phosphate and acetylcholine chloride, and significantly inhibit the degree of ears swelling in mice. As suggested from the test results of the present disclosure, Trezastilbenoside has remarkable efficacy of relieving cough, eliminating phlegm, relieving asthma and anti-inflammation, and has potential curative effects on respiratory system diseases.

2. The active ingredients of the present disclosure may can be extracted from plants, the drug materials employed are cheap and ease to be obtained easily available, and the market prospects is are promising.

In order to make the purposes, technical solutions and advantages of examples of the present disclosure clearer, hereafter the technical solutions in the examples will be described clearly and completely. The following examples are given to describe the present disclosure, but are not intended to limit the scope of the present disclosure.

DETAILED DESCRIPTION

Example 1

1. Test Materials
1.1 Animals

SPF grade ICR full-male mice (body weight: 20-24 g) and guinea pigs (body weight: 250-280 g), male and female each in half, were supplied by laboratory animal lab of KPC Pharmaceuticals, Inc., with Production License NO. SOCK (DIAN) K2014-0001. The mice were raised in IVC animal laboratory and the guinea pigs were raised in a normal grade animal room, at a temperature of 20-26° C., a humidity of 40%-70%, under the illumination in a mode of 12 h:12 h light/dark with an illumination intensity of 150-300 lx, a noise of ≥60 dB or less, and with a Laboratory Animal Use Permit NO. SYXK (DIAN) K2014-0001 issued by the Kunming Science and Technology Bureau.

1.2 Drugs and Reagents

Trezastilbenoside, with a lot number of 20160301, supplied by Research Institute of KPC Pharmaceuticals, Inc. as a raw material; Codeine phosphate tablets, produced by China National Pharmaceutical Industry Corporation Ltd. with a lot number of 20180817; Ambroxol hydrochloride tablets, produced by SANDOZ (China) Pharmaceutical Co., Ltd. with a lot number of FP264; Aminophylline tablets, produced by Shanxi Taiyuan Pharmaceutical Co., Ltd. with a lot number of 181017; Dexamethasone acetate tablets, produced by Suicheng Pharmaceutical Co., Ltd. with a lot number of 1805311; Ammonium hydroxide, AR 500 ml, with a lot number of 2018420; phenol red, 25 g, with a lot number of 20170905; sodium bicarbonate, with a lot number of 20180920 and xylene with a lot number of 20170320 all from Tianjin Fengchuan Chemical Reagent Technology Co., Ltd. Chloral hydrate, produced by Sinopharm Shanghai Chemical Reagent Co., Ltd., with a lot number of 20180529; sodium chloride injection produced, produced by Zhejiang Guojing Pharmaceutical Co., Ltd. of KELUN Pharmaceutical Group with a lot number of A160301D1; carboxy methyl cellulose sodium (CMC-Na), produced by Anhui Shanhe Pharmaceutical Excipients Co., Ltd. with a lot number of 160507; and pure water was available at any time.

1.3 Instruments

Varioskan Flash full-wavelength multifunctional microplate reader, Thermo Fisher Scientific Biofuge desktop refrigerated centrifuge, Milli-Q Integral 5 ultrapure water purification system, Thermo USA ultra-low freezers, 4021A type nebulizer made by Jiangsu Yuwell Medical Equipment Co. Ltd., AR224 type electronic balance made by OHAUS Instruments (Shanghai) Co. Ltd., BL-2000 type electronic balance made by Xiamen Balance Electronic Technology Co. Ltd., and HG-9245A type electric constant temperature blast drying oven made by Shaihai Yiheng Scientific Instruments Co. Ltd., etc.

2. Test Methods 2.1 Effects on the Cough Response of Mice Induced by Concentrated Ammonia (Antitussive Effects)

40 mice were taken and randomly divided into four groups, namely a negative control group (0.5% of CMC-Na: prepared before tests by weighting 5 g of CMC-Na into a beaker, adding 800 mL pure water thereto, stirring, heating, boiling, and cooling down, then using a measuring cylinder to adjust the volume to 1000 mL, to obtain the transparent, viscous liquid with a concentration of 0.5% for the preparation of test samples and solvent control. Such liquid prepared once and can be used for 5-7 days); a positive control group of codeine phosphate tablets at 60 mg/kg; Trezastilbenoside high dose (300 mg/kg) group; and Trezastilbenoside low dose (150 mg/kg) group. For each administration group, 0.5% CMC-Na was used for dissolving and diluting to a corresponding concentration. After the mice were acclimatized for 3 days, they were administered intragastrically once a day continuously for 7 days. The administration volume was 20 mL/kg, and 1 h after the last administration, the mice were placed one by one into a closed and dry container where the mist of 25% of concentrated ammonia was introduced into by spraying at constant pressure for 15 seconds to induce cough, then the cough latency and the number of coughs in mice during the 2-minute period were recorded thought observation.

2.2 Effects on the Cough in Guinea Pigs Induced by Citric Acid Spray (Antitussive Effects)

Healthy and sensitive guinea pigs (a pre-selection was carried out one day before the experiments, to exclude the guinea pigs which coughed less than 10 times during the five-minute period), having body weight of 250-280 g, male and female each in half were taken, and randomly divided into groups as described in 2.1. After the guinea pigs were acclimatized for 3 days, they were administered intragastrically once a day continuously for 5 days, and at the fifth day 1 hour after the administration, the guinea pigs were placed inside a 3 L sealed glass bell jar where 17.5% citric acid was sprayed into at constant pressure for 1 minute by an ultrasonic nebulizer. The cough latency and the number of coughs of the guinea pigs during the 5-minute period were recorded though observation. For guinea pigs whose latency exceeded 5 min, it was recorded as 5 min.

2.3 Effects on the Excretion Amount of Phenol Red from the Mouse Trachea (Expectorant Effects)

40 mice were taken and randomly divided into 4 groups as described in 2.1. The positive control group received ambroxol hydrochloride tablets at 20 mg/kg. After the mice were acclimatized for 3 days, they were administered intragastrically once a day continuously for 7 days. The administration volume was 20 mL/kg, and 30 min after the last administration, each mouse was intraperitoneally injected with 5% phenol red solution at 0.2 mL/20 g, sacrificed after 30 min, fixed supine, neck straightened, surrounding connective tissue stripped to expose the trachea, and dissected to separate out a section of trachea that was from below the thyroid cartilage to the bifurcation of the trachea. Each trachea section was put into a test tube pre-filled with 2 mL of 5% $NaHCO_3$ solution, ultrasonically washed for 15 min to release the tracheal phenol red out from the trachea completely, and centrifuged at 1000 r/min for 15 min to obtain a supernatant. The absorbance values of the supernatant at 546 nm were measured by an enzyme reader, and converted into the phenol red content by being compared with standard curves of phenol red.

2.4 Effects on the Allergic Asthma in Guinea Pigs (Effects for Relieving Asthma)

40 guinea pigs, male and female each in half, having body weight of 250-280 g, were randomly divided into 4 groups as described in 2.1. The positive control group received aminophylline tablets at 100 mg/kg. After the guinea pigs were acclimatized for 3 days, they received 10% fresh egg protein solution at 10 mL/kg through an intraperitoneal injection. From the $15^{th}$ day, it began to administer intragastrically to each group at 10 mL/kg. The negative control group received equal volume of 0.5% CMC-Na once per day continuously for 7 days. From the $17^{th}$ day, it began to let the guinea pigs inhale 1% egg protein solution, by spraying through an asthma-inducing, for 15 min to elicit at 1-day intervals totally for 3 times. After the last irritation, the asthma latency in the guinea pigs, that is, the time from the beginning of spray to asthma attacks (cough, dyspnea, restlessness, convulsions, falling down or death), was recorded. For the guinea pigs which had not appeared asthma attack after 6 min, their latency was taken as 6 min.

2.5 Effects on Ears Swelling of Mice Induced by Xylene (Anti-Inflammatory Effects)

40 mice were taken and randomly divided into 4 groups of 10 mice each as described in 2.1, in which intragastric administration was conducted at 10 mL/kg, the positive control group received dexamethasone acetate tablets at 5 mg/kg, and the negative control group received equal volume of 0.5% CMC-Na, once per day continuously for 7 days. At the night before the experiments, the mice were fasted but had access to water for 12 h. At the $7^{th}$ day, 30 min after the administration, the mice were evenly smeared with the inflammatory agent xylene (20 µL for each mouse) at the front and back sides of right ears to cause inflammation, and killed by cervical dislocation after 30 min, with their both ears cut along the baseline of the auricle. The ear pieces of the same part of the both ears were punched out with a hole punch of 6 mm diameter, and weighted by an analytical balance. The difference between the weights of the two ears was the swelling degree (mg), and the swelling inhibition rate (%) was calculated.

> Swelling inhibition rate=(Average swelling degree of the control group−Average swelling degree of the administration group)/Average swelling degree of the control group 2.6 Statistical Methods:

Experimental data were analyzed using SPSS17.0 software, and expressed as means±standard deviations ($\bar{x}$±SD). When the homogeneity of variance was complied, LSD test was used to make comparison between groups; and when the homogeneity of variance was not complied, Dunnett's T3 test was used to make comparison between groups. A P-value less than 0.05 means a statistical significance, and a P-value less than 0.01 means a significant statistical significance.

3. Test Results 3.1 Effects on the Cough Response of Mice Induced by Concentrated Ammonia (Antitussive Effects)

As can be seen from Table 1, as compared to the negative control group, for the codeine phosphate tablet positive control group and the Trezastilbenoside high dose group, the differences in the cough latency and the number of coughs all had statistical significance (P<0.05); and the differences of the number of coughs between the low dose group and the negative control group also had statistical significance (P<0.05), indicating that Trezastilbenoside has relatively significant antitussive effects.

TABLE 1

Effects of Trezastilbenoside on the cough response of mice induced by concentrated ammonia ($\bar{x} \pm s$, n = 10)

| Groups | Doses (mg/kg) | Latency (s) | Number of coughs per 2 min |
|---|---|---|---|
| Negative control group | — | 35.28 ± 8.36 | 36.38 ± 13.16 |
| Codeine phosphate tablets | 60 | 56.23 ± 16.46* | 15.13 ± 7.83* |
| Trezastilbenoside | 150 | 41.23 ± 13.67 | 25.88 ± 9.25* |
| Trezastilbenoside | 300 | 48.56 ± 16.53* | 19.63 ± 10.27* |

*P-value less than 0.05 as compared to the negative control group.

3.2 Effects on the Cough in Guinea Pigs Induced by Citric Acid Spray

As can be seen from Table 2, either a high dose or a low dose of Trezastilbenoside was able to significantly prolong the cough latency in guinea pigs induced by citric acid spray (P<0.05), and significantly reduce the number of coughs during the 5-minute period (P<0.05).

TABLE 2

Effects of Trezastilbenoside on the cough response of mice reduced by citric acid spray ($\bar{x} \pm s$, n = 10)

| Groups | Doses (mg/kg) | Latency (s) | Number of coughs per 5 min |
|---|---|---|---|
| Negative control group | | 84.28 ± 19.16 | 16.38 ± 6.16 |
| Codeine phosphate tablet | 60 | 130.48 ± 59.34** | 7.83 ± 3.83** |
| Trezastilbenoside | 150 | 104.35 ± 45.23* | 13.88 ± 5.25* |
| Trezastilbenoside | 300 | 116.78 ± 53.96* | 9.63 ± 3.20* |

*P-value less than 0.05,
**P-value less than 0.01, as compared to the negative control group.

3.3 Effects on the Excretion Amount of Phenol Red from the Mouse Trachea

As can be seen from Table 3, as compared to the control group, the secretion and discharge of phenol red by the trachea cilia of mice in the Trezastilbenoside high dose group and in the positive control group were all promoted significantly, indicating a good expectorant effect, and there were significant differences as compared to the negative control group (P<0.05).

TABLE 3

Effects of Trezastilbenoside on the excretion amount of phenol red from the mouse trachea ($\bar{x} \pm s$, n = 10)

| Groups | Doses (mg/kg) | Phenol red concentration ($\mu g \cdot mL^{-1}$) |
|---|---|---|
| Negative control group | | 2.89 ± 0.96 |
| Ambroxol hydrochloride tablet | 20 | 4.23 ± 1.34* |
| Trezastilbenoside | 150 | 3.28 ± 1.20 |
| Trezastilbenoside | 300 | 3.88 ± 1.43* |

*P-value less than 0.05, as compared to the negative control group.

3.4 Effects on the Allergic Asthma in Guinea Pigs

As can be seen from Table 4, as compared to the negative control group, the latencies of asthma attacks during the 6-minute period in guinea pigs in the Trezastilbenoside high dose group and low dose group, were both prolonged significantly (P<0.05 or 0.01), and appeared to correlate with the dose. The effects of the Trezastilbenoside high dose group were comparable to that of the positive control of aminophylline tablets.

TABLE 4

Effects of Trezastilbenoside on guinea pigs allergic asthma

| Groups | Doses (mg/kg) | Latency (s) |
|---|---|---|
| Negative control group | | 52.46 ± 22.96 |
| Aminophylline tablet | 100 | 94.23 ± 31.55** |
| Trezastilbenoside | 150 | 69.28 ± 21.20* |
| Trezastilbenoside | 300 | 83.68 ± 36.13** |

*P-value less than 0.05,
**P-value less than 0.01, as compared to the negative control group 3.5 Effects on the Ears Swelling of Mice Induced by Xylene As can be seen from Table 5, as compared to the negative control group, the ears swelling degree of mice in the Trezastilbenoside high dose group and the positive control group were both reduced significantly (P<0.05 or 0.01). In the low dose group, there was a tendency of anti-inflammation, but no statistical difference.

TABLE 5

Effects of Trezastilbenoside on the ears swelling of mice induced by xylene

| Groups | Doses (mg/kg) | Swelling degree (mg) | Swelling inhibition rate (%) |
|---|---|---|---|
| Negative control group | | 3.64 ± 2.32 | |
| Dexamethasone acetate tablet | 5 | 1.24 ± 0.67** | 65.93 |
| Trezastilbenoside | 150 | 3.12 ± 2.52 | 14.28 |
| Trezastilbenoside | 300 | 2.21 ± 1.45* | 39.29 |

*P-value less than 0.05,
**P-value less than 0.01, as compared to the negative control group.

Example 2

In this example, the tablets were consisted of the following components: 50 g of Trezastilbenoside, 100 g of microcrystalline cellulose, 50 g of pregelatinized starch, 40 g of low substituted hydroxypropyl methylcellulose, and 1 g of micropowder silica gel.

The above raw materials were mixed to obtain the Trezastilbenoside tablets in accordance with a conventional preparation method.

Example 3

In this example, the capsules were consisted of the following components: 25 g of Trezastilbenoside, 80 g of microcrystalline cellulose, 10 g of lactose, a proper amount of povidone K-30, and 2 g of magnesium stearate.

The above raw materials were mixed to obtain the Trezastilbenoside capsules in accordance with a conventional preparation method.

Example 4

In this example, the granules were consisted of the following components: 50 g of Trezastilbenoside, 100 g of mannitol, 100 g of lactose, 2 g of sodium cyclamate, 1 g of solid edible essence, 2 g of xanthan gum, and a proper amount of 8% povidone K-30 ethanol aqueous solution.

The above raw materials were mixed to obtain the Trezastilbenoside granules in accordance with a conventional preparation method.

Example 5

In this example, the dropping pills were consisted of the following components: 5 g of Trezastilbenoside and 15 g of polyethylene glycol 6000.

The above raw materials were mixed to obtain the Trezastilbenoside dropping pills in accordance with a conventional preparation method.

The above descriptions are merely the preferred embodiments of the present disclosure, and are not intended to limit the present disclosure in any form. Though the present disclosure has been disclosed by using the preferred embodiments as above, it is not intended to limit the present disclosure. It is possible for any one skilled in the art to make some amendments and modifications to obtain equivalent variations of the examples by utilizing the technical contents mentioned above, without departing from the scope of the technical solutions of the present disclosure. However, anything that does not departed from the technical solutions of the present disclosure, including any simple amendments, equivalent variations and modifications, should fall within the scope of technical solutions of the present disclosure.

The invention claimed is:

1. A method of treating a disease of respiratory system with a cough symptom, comprising administering trezastilbenoside to a subject in need thereof, wherein the cough symptom is induced by inhalation.

2. The method of claim 1, wherein trezastilbenoside is provided as a food product, a health product or a medicament.

3. The method of claim 1, wherein trezastilbenoside is provided as a medicament, comprising trezastilbenoside and a pharmaceutically acceptable adjuvant.

4. The method of claim 3, wherein the medicament is provided as various acceptable dosage forms.

5. The method of claim 4, wherein the dosage forms include injections, tablets, capsules, powders, pills, oral solutions or suspensions.

* * * * *